United States Patent [19]

Gaffney et al.

[11] Patent Number: 5,171,921
[45] Date of Patent: Dec. 15, 1992

[54] PRODUCTION OF OLEFINS

[75] Inventors: Anne M. Gaffney; John A. Sofranko, both of West Chester, Pa.

[73] Assignee: Arco Chemical Technology, L.P., Wilmington, Del.

[21] Appl. No.: 692,333

[22] Filed: Apr. 26, 1991

[51] Int. Cl.$^5$ .............................................. C07C 4/02
[52] U.S. Cl. .................................................. 585/653
[58] Field of Search ...................................... 585/653

[56] References Cited

U.S. PATENT DOCUMENTS

| | | | |
|---|---|---|---|
| 4,044,065 | 8/1977 | Butter et al. | 585/653 |
| 4,356,338 | 10/1982 | Young | 585/407 |
| 4,423,266 | 12/1983 | Young | 585/466 |

FOREIGN PATENT DOCUMENTS 60-222428  11/1985  Japan.

Primary Examiner—Patrick P. Garvin
Assistant Examiner—E. D. Irzinski
Attorney, Agent, or Firm—William C. Long

[57] ABSTRACT

A steam activated catalyst containing phosphorus and H-ZSM-5 may be used to convert higher hydrocarbons to lower olefins, especially ethylene, propylene, butylenes and pentenes at a preferred temperature range of 500° to 700° C. and a preferred WHSV range of 10 to 1000 hr.$^{-1}$. Catalysts containing H-ZSM-5 with surface Si/Al ratios of 20 to 60 were found to undergo steam activation more readily and achieve higher activity than those catalysts which contained H-ZSM-5 with surface Si/Al ratios greater than 60.

5 Claims, No Drawings

PRODUCTION OF OLEFINS

BACKGROUND OF THE INVENTION

1. Field of the Invention

The present invention relates to the production of lower olefins such as ethylene, propylene, butenes and pentenes from higher hydrocarbons by contacting the higher hydrocarbon feed with a particular ZSM-5 zeolite catalyst which has a surface Si/Al ratio of 20 to 60, which contains phosphorus and which has been steam treated after phosphorus addition The contact is carried out at conditions which favor lower olefin formation including high space velocity of at least 50 hr$^{-1}$ WHSV, high temperature, low conversion per pass and low hydrocarbon partial pressure.

2. Description of the Prior Art

Methods are currently known for the production of commercially important olefins such as ethylene, propylene, butenes and pentenes from paraffinic feed materials. Such methods include steam cracking, propane dehydrogenation and various refinery catalytic cracking operations.

Each of these procedures has certain disadvantages. For example, propylene yields from steam cracking are not very high and are not substantially improved by recycling. Purification of non-propylene products is required which is costly or such products have only fuel value.

Propane dehydrogenation processes are characterized by rapid catalyst coking requiring frequent, costly regenerations. Also, reasonable conversions require sub-atmospheric pressures, and propane is difficult to separate from propylene.

Propylene supplies from catalytic conversions are uncertain. Transportation and purification are significant problems.

Methods are known for the production of lower olefins from higher hydrocarbon feedstocks. Copending application Ser. No. 07/500,172 filed Mar. 27, 1990 describes an improved process for the formation of lower olefins from mixtures of paraffins and olefins using zeolite catalysts including phosphorus containing zeolites.

European 0 109059 shows the production of lower olefins from higher hydrocarbons at high temperature and high space velocity using zeolite catalysts.

U.S. Pat. Nos. 3,972,832 and 4,044,065 show hydrocarbon conversions using a phosphorus-containing zeolite such as ZSM-5.

U.S. Pat. Nos. 4,356,338 and 4,423,266 show that zeolite catalysts can be advantageously treated with phosphorus and/or steam.

U.S. Pat. Nos. 4,559,314 and 4,784,747 show that zeolite activity can be improved by forming the catalyst into a composite with a binder such as alumina and steaming the composite.

SUMMARY OF THE INVENTION

The present invention provides an improved process for the production of $C_2$-$C_5$ olefins from higher olefinic or paraffinic or mixed olefin and paraffin feedstocks. In accordance with the invention, the hydrocarbon feed materials are contacted with a particular ZSM-5 catalyst at elevated temperatures, high space velocity and low hydrocarbon partial pressure to produce lower olefins. The catalyst which is employed is ZSM-5 having a surface Si/Al ratio in the range 20 to 60 and a phosphorus content of 0.1 to 10 wt. %. The catalysts is treated with steam prior to use in the hydrocarbon conversion.

DETAILED DESCRIPTION OF THE INVENTION

In accordance with the present invention, higher hydrocarbons are converted to the more valuable lower $C_2$-$C_5$ olefins. Generally, paraffins, olefins and mixtures of paraffins and olefins having 3 to 20 carbon atoms, preferably 4 to 12 carbon atoms comprise suitable feed materials.

The feed mixture may also contain aromatics, napthenes and inerts such as nitrogen, but the benzene content should not exceed 30 wt. % of the total feed. At benzene concentrations above 40 wt. %, alkylation becomes significant, and light olefin yields are reduced. The feed mixture may also contain steam in amount up to 30 mol. %, preferably 1 to 20 mol. %.

The hydrocarbon conversion is carried out at condiitions which favor the formation of lower olefins. Reaction temperatures broadly in the range 300° to 1000° C. can be employed, although the preferred temperature range is 500°–700° C.

The hydrocarbon feed weight hourly space velocity (based on the ZSM-5 component of the catalyst) must be quite high in order to accomplish the efficient conversion to lower olefins. Weight hourly space velocities in the range 50–1000 hr.$^{-1}$, preferably 50–500 hr.$^{-1}$ are suitable.

Low hydrocarbon partial pressures and low conversions per pass favor lower olefin production. The feed hydrocarbon can be admixed with steam or inert gas such as nitrogen. The hydrocarbon partial pressure is as low as practical, illustratively 1 to 30 psia. Where no diluents are employed, system pressures ranging from about $-12$ to 50 psig, preferably $-5$ to 30 psig, are suitable. Higher pressures can be used when diluents are employed.

High space velocity as above indicated and short residence times are preferred in order to maintain the desired low conversions per pass. Paraffin hydrocarbon conversions per pass are less than 50%. Reactor residence times are 0.001 to 20 seconds, preferably 0 01 to 5 seconds.

The conversion reaction of the instant invention is highly endothermic. Preferably fluidized solid catalyst conversion procedures are used with the feed hydrocarbon vapor contacting fluidized particles of the zeolite catalyst. Heat necessary to maintain the reaction is provided by separately heating the catalyst particles in a fluidized regeneration zone as by combustion of appropriate fuel hydrocarbon.

Fixed bed procedures can be employed. In such cases, the use of reaction zones in series with interstage heating is advantageous.

The catalyst which is employed forms a critical feature of the present invention. The active catalyst component is phosphorus-containing ZSM-5 having a surface Si/Al ratio in the range 20–60. Preferably, the phosphorus is added to the formed ZSM-5 as by impregnating the ZSM-5 with a phosphorus compound in accordance with the procedures described, for example, in U.S. Pat. No. 3,972,832. Less preferably, the phosphorus compound can be added to the multicomponent mixture from which the catalyst is formed. The phosphorus compound is added in amount sufficient to provide a final ZSM-5 composition having 0.1-10 wt. % phosphorus, preferably 1-3 wt. %.

The phosphorus-containing ZSM-5 is preferably combined with known binders or matrices such as silica, kaolin, calcium bentonite, alumina, silica aluminate and the like. The ZSM-5 generally comprises 1-50 wt. % of the catalyst composition, preferably 5-30 wt. % and most preferably 10-25 wt. %.

The surface Si/Al ratio is 20-60. Most conveniently, this is achieved by regulation of the amounts of the components which are used in formulation of the zeolite in accordance with known procedures.

In general, the ZSM-5 is ordinarily ion exchanged with a desired cation to replace alkali metal present in the zeolite as prepared. The exchange treatment is such as to reduce the alkali metal content of the final catalyst to less than about 0.5 weight percent, and preferably less than about 0.1 weight percent. The preferred proton source is ammonium chloride as opposed to hydrochoric acid, sulfuric acid and nitric acid. Ion exchange is suitably accomplished by conventional contact of the zeolite with an aqueous solution of the proton source.

A further important feature of the invention is the activation of the ZSM-5 catalyst with steam after incorporation of phosphorus therein. The steam treatment is best carried out as a discrete step prior to use of the catalyst in hydrocarbon conversion. The preferred method is to heat the catalyst at 500° to 700° C., preferably 550° to 600° C., under 1 to 5 atmospheres, preferably 1.5 to 3 atmospheres steam for 1 to 48 hours, preferably 15 to 30 hours. An alternative method is to add about 1 to 50 mol. % steam to the hydrocarbon feed during hydrocarbon conversion. This method calls for a longer time to achieve activation of the catalyst and thus is not preferred.

It should be noted that even where the catalyst is steam treated in a discrete step prior to hydrocarbon conversion, it is preferred to employ 1 to 50 mol. % steam in the feed, preferably 2 to 20 mol. % steam to obtain further improvements in activity.

COMPARATIVE EXAMPLES

The catalytic cracking activity of four protonated pentasil H-ZSM-5 catalysts was determined for butene −2 cracking. The four catalysts were of nearly comparable bulk Si/Al ratio, the Si/Al ratios varying from 38.18 to 44.79. The cracking procedure was as follows:

A tubular reactor is packed with 0.02 g. of the protonated pentasil diluted with 1.00 g. of alpha alumina. The reactor is then placed in a tubular furnace. Air is passed through the catalyst bed at 100 cc/minute and the catalyst bed temperature is increased to 600° C. A nitrogen purge of 100 cc/minute is passed through the catalyst bed for five minutes after which time the 2-butene feed is passed over the catalyst bed. After one minute into the run, the effluent stream is sampled instantaneously by a gas tight syringe. This sample is then injected into a gas chromatograph equipped with a PLOT column and flame ionization detector. By this analytical method the extent of 2-butene conversion to $C_1$ to $C_{10}$ hydrocarbons is determined. Following the 2-butene run, a nitrogen purge at 100 cc/minute for five minutes is carried out. Subsequently, an air regeneration for ten minutes at 100 cc/minute is carried out. During the air regeneration, the total effluent stream is collected in a gas sampling bag. Following the air regeneration, the contents of the gas bag are analyzed on a gas chromatograph equipped with a concentric molecular sieve and Poropak Q column and thermal conductivity detector. By this method the amounts of $CO_2$ and CO, which are the oxidized coke products, are determined. The combined analytical results give the total 2-butene conversion and the product selectivity slate to $C_1$ to $C_8$ hydrocarbons and coke. The results are calculated on a $C_1$ molar basis.

Cracking results obtained for each of the four catalysts together with the bulk Si/Al ratio and relative cracking activity for each is shown in Table 1 and 2.

TABLE 1

| H-ZSM-5 Catalyst | A | B | C | D |
|---|---|---|---|---|
| Bulk Si/Al Ratio | 38.18 | 44.21 | 44.79 | 42.86 |
| Relative Activity | 2.80 | 1.00 | 1.00 | 0.90 |
| WHSV hr$^{-1}$ | 2200 | 800 | 780 | 683 |
| Temp °C. | 600 | 600 | 600 | 600 |
| % $C_4^=$ Conv. | 60.00 | 51.00 | 59.00 | 59.50 |
| % Sel. To: | | | | |
| $CH_4$ | 0.09 | 0.29 | 0.20 | 0.2 |
| $C_2$ | 0.09 | 0.13 | 0.12 | 0.14 |
| $C_2^=$ | 10.00 | 13.80 | 11.70 | 11.80 |
| $C_3$ | 1.70 | 1.30 | 1.50 | 1.70 |
| $C_3^=$ | 49.00 | 54.90 | 50.80 | 49.70 |
| iso-butane | 2.10 | 2.70 | 2.50 | 2.80 |
| n-butane | 7.40 | 4.60 | 6.00 | 4.50 |
| butadiene | 0.31 | 0.33 | 0.30 | 0.24 |
| $C_5$ | 19.60 | 17.30 | 19.00 | 19.40 |
| $C_6^+$ | 9.60 | 4.80 | 7.70 | 9.60 |
| Coke | 0.10 | 0.22 | 0.18 | 0.08 |

TABLE 2

ELEMENTAL AND ACTIVITY OF PENTASILS

| H-ZSM-5 | ICP WT % | Si/AL | RELATIVE ACTIVITY 2-Butene CONV. |
|---|---|---|---|
| A | Si 42<br>Al 1.1<br>Na 0.007<br>Cl < 20 ppm | 38.18 | 2.8 |
| B | Si 42<br>Al 0.95<br>Na < 0.002<br>Cl < 20 ppm | 44.21 | 1.0 |
| C | Si 43<br>Al 0.96<br>Na 0.028<br>Cl < 20 ppm | 44.79 | 1.0 |
| D | Si 42<br>Al 0.98<br>Na < 0.001<br>Cl < 20 ppm | 42.86 | 0.9 |

$^1$H MAS NMR indicated catalytic activity increased with increased amount of bridging hydroxyl groups, i.e. increased number of Bronstead acid sites. These spectoscopic results are shown in Table 3. ESCA analysis indicated that, in general, catalytic activity increased as the surface Si/Al ratio of the protonated pentasil deceased and approached the value of the corresponding bulk Si/Al ratio. These results are shown in Table 4. In conclusion, in these comparative runs, the preferred protonated pentasil is one in which both the bulk and surface Si/Al ratios are nearly equivalent and close to 40 and simultaneously the number of Bronstead acid sites is sufficiently high (% area at 4 ppm > 20).

TABLE 3

| | $^1$H MAS NMR |
|---|---|
| H-ZSM-5 Catalyst | A<br>% Area, 4 ppm |
| A | 32.54 |
| B | 18.30 |
| C | 7.59 |

TABLE 3-continued

| H-ZSM-5 Catalyst | ¹H MAS NMR<br>A<br>% Area, 4 ppm |
|---|---|
| D | 3.68 |

A - ASSIGNED TO BRIDGING HYDROXYL GROUPS
The percent area under the peak at 4 ppm is proportional to the number of Bronstead acid sites.

TABLE 4

| H-ZSM-5 Catalyst | ESCA<br>Si/Al "Surface Ratio" |
|---|---|
| A | 36.4 |
| B | 55.9 |
| C | 43.1 |
| D | 74.5 |

EXAMPLE 1

Catalysts were prepared using protonated pentasil B as described in the above comparative example. In the case of Catalyst E, phosphoric acid was added to the pentasil by incipient wetness to incorporate about 1% by weight phosphorus based on the catalyst. The phosphorus-containing pentasil was dried and slurried in water with silica, calcium bentonite and kaolin and spray dried to form a catalyst comprised of 26 wt. % phosphorus-containing pentasil, 2 wt. % calcium bentonite, 25 wt. % silica and the balance kaolin. The catalyst was calcined in air and subsequently hydrothermally activated by heating overnight at 2 atms in steam at 550° C. In the case of Catalyst F, the phosphoric acid was added to the aqueous slurry with the pentasil, silica, calcium bentonite and kaolin in amount of 3 wt. % based on the catalyst as phosphorus, the slurry was spray dried to form a catalyst comprised of 25 wt. % pentasil, 3 wt. % phosphorus, 25 wt. % silica, 2 wt. % calcium bentonite and the balance kaolin. Catalyst F was calcined and hydrothermally treated in the same manner as Catalyst E.

Catalysts E and F were tested both before and after the hydrothermal treatment for butene-2 cracking activity by the method described above in the comparative example. Results are given in Table 5.

As shown in the following table, best results were obtained from a catalyst prepared by procedures that called for direct phosphorus addition to the pentasil prior to adding other catalyst components such as silica, calcium bentonate and kaolin. Catalyst E underwent hydrothermal activation readily and gave the desired cracking activity. Whereas, catalyst preparation procedures which called for phosphorus addition in the presence of all catalyst components such as the pentasil, silica, calcium benonite and kaolin did not steam activate readily and had inferior cracking activity. Note that both Catalyst E and F contain 25 wt. % pentasil. For Catalyst E, 1 wt. % phosphorus was added directly to the zeolite. Whereas for Catalyst F, 3 wt. % phosphorus was added to the overall slurry composition. Direct phosphorus addition to the pentasil is preferred since this facilitates phosphorus framework incorporation which leads to enhanced hydrothermal stability and catalytic activity. Non-direct addition of phosphorus to the catalyst slurry results in some phosphorus reacting with the silica, calcium bentonite and kaolin.

TABLE 5

| | Catalyst | | | |
|---|---|---|---|---|
| | Catalyst E Prior to Hydrothermal Activation | Catalyst E After Hydrothermal Activation | Catalyst F Prior to Hydrothermal Activation | Catalyst F After Hydrothermal Activation |
| Temp. °C. | 600 | 600 | 600 | 600 |
| WHSV, hr⁻¹ | 31 | 125 | 10 | 21 |
| % C₄⁼ Conv. | 60 | 65 | 25 | 28 |
| % Sel. to: | | | | |
| CH₄ | 0.21 | 0.11 | 0.40 | 0.42 |
| C₂ | 0.12 | 0.09 | 0.06 | 0.08 |
| C₂⁼ | 11.20 | 8.70 | 1.80 | 3.80 |
| C₃ | 1.10 | 1.40 | 0.12 | 0.31 |
| C₃⁼ | 49.00 | 49.90 | 17.40 | 27.30 |
| iso-butane | 2.00 | 1.80 | 0.60 | 0.89 |
| n-butane | 5.40 | 5.80 | 11.00 | 10.20 |
| butadiene | 0.33 | 0.26 | 1.00 | 0.89 |
| C₅ | 17.40 | 18.10 | 33.70 | 30.70 |
| C₆⁺ | 12.10 | 23.80 | 33.40 | 24.80 |
| Coke | 0.20 | 0.06 | 0.59 | 0.60 |

EXAMPLE 2

The following example demonstrates the positive effects of phosphorus and steam on the pentasil containing cracking catalyst. Catalyst E prepared as above described, contains 25 wt. % pentasil, 25 wt. % silica, 2 wt. % calcium bentonite, 45 wt. % kaolin and 1 wt. % phosphorus. Its 2-butene cracking activity increased fourfold after hydrothermal treatment Catalyst G has the same composition except phosphorus has been excluded. Its 2-butene cracking activity decreased twofold after hydrothermal treatment. The hydrothermally treated Catalyst G was four times less active than the hydrothermally treated Catalyst E. These results are shown in table 6. Note that resistance to steam deactivation is important for catalyst performance and life. Most catalytic cracking units operate in the presence of steam and steam is generated in-situ during coke burn-off. Cracking procedures were as described in the above comparative example.

TABLE 6

| | Catalyst E Prior to Hydrothermal Activation | Catalyst E After Hydrothermal Activation | Catalyst G Prior to Hydrothermal Activation | Catalyst G After Hydrothermal Activation |
|---|---|---|---|---|
| Temp. °C. | 600 | 600 | 600 | 600 |
| WHSV, hr⁻¹ | 31 | 125 | 62.5 | 31 |
| % C₄⁼ Conv. | 60 | 65 | 57 | 58 |
| % Sel. to: | | | | |
| CH₄ | 0.21 | 0.11 | 0.91 | 1.30 |
| C₂ | 0.12 | 0.09 | 0.19 | 0.31 |
| C₂⁼ | 11.20 | 8.70 | 14.20 | 18.00 |
| C₃ | 1.10 | 1.40 | 1.60 | 1.80 |
| C₃⁼ | 49.00 | 49.90 | 52.00 | 55.70 |
| iso-butane | 2.00 | 1.80 | 3.30 | 3.30 |
| n-butane | 6.40 | 5.80 | 5.10 | 4.50 |
| butadiene | 0.33 | 0.26 | 0.27 | 0.31 |
| C₅ | 17.40 | 18.10 | 14.60 | 9.40 |
| C₆⁺ | 12.10 | 23.80 | 7.90 | 5.40 |
| Coke | 0.20 | 0.06 | 0.11 | 0.44 |

EXAMPLE 3

The following example demonstrates the superiority of Catalyst E over Catalyst F for the cracking of UDEX raffinate to lower olefins. Note that Catalyst E called for direct phosphorus addition to the H-ZSM-5 while for Catalyst F phosphorus was added to the slurry.

Results are shown in Table 7. Data in Table 7 indicates catalyst E is approximately twice as active as Catalyst F.

TABLE 7

30 Minute UDEX Raffinate Runs

|  | Catalyst F After Hydrothermal Activation | Catalyst E After Hydrothermal Activation |
|---|---|---|
| Temp. °C. | 620 | 620 |
| WHSV, hr$^{-1}$ | 32 | 30 |
| % Conv. | 18.0 | 35.5 |
| % Sel. to: | | |
| CH$_4$ | 6.5 | 5.5 |
| C$_2$ | 5.9 | 7.6 |
| C$_2$= | 13.8 | 18.6 |
| C$_3$ | 1.9 | 5.3 |
| C$_3$= | 45.0 | 42.8 |
| iso-butane | 0.2 | 0.6 |
| n-butane | 0.4 | 1.1 |
| butadiene | 0.3 | 0.2 |
| Butenes | 11.4 | 14.9 |
| C$_5$ Olefins | 13.3 | 3.1 |
| C$_8$+ | 1.0 | 0.2 |
| Coke | 0.3 | 0.1 |

EXAMPLE 4

Catalyst E was 70% more active than Catalyst F for the cracking of n-octane as shown in Table 8.

TABLE 8

Two Hour n-Octane Runs

|  | Catalyst E After Hydrothermal Activation | Catalyst F After Hydrothermal Activation |
|---|---|---|
| Temp. °C. | 650 | 650 |
| WHSV, hr$^{-1}$ | 67 | 67 |
| % Conv. | 46.5 | 27.4 |
| % Sel to: | | |
| CH$_4$ | 6.1 | 5.2 |
| C$_2$ | 9.1 | 7.4 |
| C$_2$= | 24.3 | 19.7 |
| C$_3$ | 1.2 | 1.8 |
| C$_3$= | 26.2 | 25.8 |
| iso-butane | 0.01 | 0.01 |
| n-butane | 0.6 | 1.1 |
| butadiene | 0.5 | 0.2 |
| Butenes | 15.2 | 19.2 |
| C$_5$ Olefins | 1.8 | 11.4 |
| C$_5$ Paraffins | 10.7 | 1.7 |
| C$_6$ | 2.7 | 3.4 |
| C$_7$ | 0.5 | 0.4 |
| C$_8$ Olefins | 0.9 | 2.2 |
| C$_9$ | 0.02 | 0.2 |
| C$_{10}$ | 0 | 0 |
| Coke | 0 | 0 |

EXAMPLE 5

Cracking of 2-butene was carried out over steam treated H-ZSM-5 pentasils containing phosphorus. H-ZSM-5, Catalyst A from the comparative example was impregnated with phosphorus and steam treated as described in Example 1. This catalyst was three times more active than Catalyst D, H-ZSM-5, which was also impregnated with phosphorus and steam treated. Note that Catalyst A has a surface Si/Al ratio of 36.4, whereas Catalyst D has a surface Si/Al ratio of 74.5. A lower ratio is more conducive to phosphorus incorporation into the framework during steam treatment. Results are shown in Table 9.

TABLE 9

Conditions: 2-Butene conversion, 600° C., 60 sec. run, 10 minute air regeneration.

|  | Catalyst A Containing Phosphorus Hydrothermally Treated | Catalyst D Containing Phosphorus Hydrothermally Treated |
|---|---|---|
| Surface Si/Al Ratio | 36.4 | 74.5 |
| WHSV, hr$^{-1}$ | 366 | 110 |
| % Conv. C$_4$= | 59.5 | 62.5 |
| % Sel. to: | | |
| CH$_4$ | 0.17 | 0.19 |
| C$_2$ | 0.10 | 0.12 |
| C$_2$= | 10.9 | 12.2 |
| C$_3$ | 1.6 | 1.5 |
| C$_3$= | 49.7 | 50.2 |
| isobutane | 2.4 | 1.9 |
| n-butane | 4.8 | 6.2 |
| butadiene | 0.27 | 0.35 |
| C$_5$ | 18.9 | 14.7 |
| C$_6$+ | 11.1 | 12.5 |
| Coke | 0.04 | 0.10 |

What is claimed is:

1. The method of converting paraffin, olefin and mixtures of paraffin and olefin hydrocarbons having 3 to 20 carbon atoms to C$_2$–C$_5$ olefins which comprises contacting the C$_3$–C$_{20}$ hydrocarbons at 300°–1000° C. and 10–1000 hr.$^{-1}$ WHSV with a catalyst comprised of steam activated ZSM-5 having a surface Si/Al ratio of 20–60, and containing 0.1–10 wt. % phosphorus, said ZSM-5 being steam activated at 500°–700° C. after incorporation of said phosphorus therein.

2. The method of claim 1 wherein the ZSM-5 contains 1–3 wt. % phosphorus.

3. The method of claim 1 wherein the ZSM-5 comprises 1–50 wt. % of the catalyst.

4. The method of claim 1 wherein the ZSM-5 comprises 1–50 wt. % of the catalyst and is pretreated with phosphorus before being combined with binders and matrices.

5. The method of claim 1 wherein the ZSM-5 is steam activated at 500°–700° C. under 1–5 atmospheres steam for 1 to 48 hours.

* * * * *